United States Patent
Hessefort et al.

(10) Patent No.: US 7,455,848 B2
(45) Date of Patent: *Nov. 25, 2008

(54) SKIN CARE COMPOSITION CONTAINING AN ANIONIC POLYMER

(75) Inventors: Yin Z. Hessefort, Naperville, IL (US); Douglas Betts, Durham, NC (US); Wayne M. Carlson, Batavia, IL (US); Loralei Brandt, St. Charles, IL (US); Jennifer L. Smith, Lemont, IL (US)

(73) Assignee: Nalco Company, Naperville, IL (US)

( * ) Notice: Subject to any disclaimer, the term of this patent is extended or adjusted under 35 U.S.C. 154(b) by 571 days.

This patent is subject to a terminal disclaimer.

(21) Appl. No.: 10/323,217

(22) Filed: Dec. 18, 2002

(65) Prior Publication Data

US 2005/0129653 A1    Jun. 16, 2005

(51) Int. Cl.
*A61Q 19/10* (2006.01)
*A61Q 1/10* (2006.01)
*A61Q 15/00* (2006.01)
*A61Q 17/04* (2006.01)

(52) U.S. Cl. .................. 424/401; 424/59; 424/65; 424/70.7

(58) Field of Classification Search ............... None
See application file for complete search history.

(56) References Cited

U.S. PATENT DOCUMENTS

| 4,065,422 | A | | 12/1977 | Lundmark et al. |
|---|---|---|---|---|
| 4,401,650 | A | | 8/1983 | Salamone |
| 5,413,775 | A | | 5/1995 | Hatfield et al. |
| 5,519,063 | A | * | 5/1996 | Mondet et al. ............ 514/772.4 |
| 5,620,683 | A | | 4/1997 | Tong et al. |
| 6,569,413 | B1 | * | 5/2003 | Hessefort et al. ......... 424/70.11 |

FOREIGN PATENT DOCUMENTS

| EP | 0 197 649 | | 5/1990 |
|---|---|---|---|
| EP | 0 503 853 | B1 | 9/1992 |
| EP | 0 522 756 | | 1/1996 |
| JP | 2002 080320 | | 3/2002 |
| WO | 02/083089 | | 10/2002 |
| WO | 02/094209 | A2 | 11/2002 |

OTHER PUBLICATIONS

Supplementary European Search Report, Application No. EP 03776404, Patent No. PCT/US0332635, filed Oct. 15, 2003. This is submitted because there is no readily available translation of WO 02/094209 A2, which is listed above.

* cited by examiner

*Primary Examiner*—Jyothsna A Venkat
(74) *Attorney, Agent, or Firm*—Peter A. DiMattia; Michael B. Martin

(57) ABSTRACT

A cosmetically acceptable composition for treating skin comprising about 0.1 to about 20 weight percent, based on polymer solids, of an anionic polymer composed of from about 10 to about 80 mole percent of 2-acrylamido-2-methyl-1-propanesulfonic acid or a base addition salt thereof and from about 90 to about 20 mole percent of one or more anionic or nonionic monomers.

13 Claims, No Drawings

SKIN CARE COMPOSITION CONTAINING AN ANIONIC POLYMER

TECHNICAL FIELD

This invention relates to compositions and methods for treating skin. More particularly, this invention concerns a cosmetically acceptable composition containing a copolymer of 2-acrylamido-2-methyl-1-propanesulfonic acid or a base addition salt thereof and one or more anionic or nonionic monomers and a method of using the composition for treating skin.

BACKGROUND OF THE INVENTION

Market research has shown a rapidly growing demand for skin care products that offer a silky or non-greasy feel. These attributes create a fresh, soft sensation that is pleasant to the user.

A large variety of skin care products are formulated in high molecular weight alcohols such as cetyl or stearyl alcohol, where the alcohol is used not only as a carrier but also to give an emollient effect upon the skin. Emollients are lipid substances used to relieve the symptoms of dryness of skin. The effect of emollients is based primarily on their capacity to leave a thin lipid film of limited water permeability on the skin. However, emollients might not deliver a silky or slippery feel to the skin upon the application of the skin care products.

A composition for treating hair and skin that contains an alcohol and 2-acrylamidopropane sulfonic acid salt homopolymer is disclosed in U.S. Pat. No. 4,065,422. The composition is said to impart a feeling of lubricity to the skin.

A hair fixative composition containing a copolymer of 2-acrylamido-2-methyl-1-propanesulfonic acid or a base addition salt thereof and one or more anionic or nonionic monomers is disclosed in PCT US02/08620.

It is an object of this invention to develop new skin care compositions that impart a feeling of lubricity or silkiness to the skin.

SUMMARY OF THE INVENTION

We have discovered that skin care compositions containing water-soluble anionic copolymers of 2-acrylamido-2-methyl-1-propanesulfonic acid provide a feeling of lubricity or silkiness to the skin. In addition, such compositions also indirectly soften and increase the flexibility of the skin.

Accordingly, this invention is a cosmetically acceptable composition for treating skin comprising about 0.1 to about 20 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic or nonionic monomers.

DETAILED DESCRIPTION OF THE INVENTION

Definitions of Terms

"Anionic monomer" means a monomer as defined herein which possesses a net negative charge above a certain pH value. Representative anionic monomers include base addition salts of acrylic acid, methacrylic acid, itaconic acid, 2-acrylamido-2-methyl-1-propanesulfonic acid, sulfopropyl acrylate or methacrylate or other water-soluble forms of these or other polymerizable carboxylic or sulfonic acids, sulphomethylated acrylamide, allyl sulphonate, styrene sulfonic acid, sodium vinyl sulphonate, and the like. Preferred anionic monomers are acrylic acid and 2-acrylamido-2-methyl-1-propanesulfonic acid.

"Base addition salt" means the salt resulting from reaction of a carboxylic acid ($-CO_2H$) group with a suitable base such as the hydroxide, carbonate, or bicarbonate of a metal cation or tetraalkylammonium cation, or with ammonia, or an organic primary, secondary, or tertiary amine of sufficient basicity to form a salt with the carboxylic acid group. Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. Preferred base addition salts include the sodium and ammonium salts.

"IV" stands for intrinsic viscosity, which is RSV extrapolated to the limit of infinite dilution, infinite dilution being when the concentration of polymer is equal to zero.

"Monomer" means a polymerizable allylic, vinylic or acrylic compound. The monomer may be anionic, cationic or nonionic. Vinyl monomers are preferred, acrylic monomers are more preferred.

"Nonionic monomer" means a monomer as defined herein which is electrically neutral. Representative non-ionic, water-soluble monomers include acrylamide, methacrylamide, N,N-dimethylacrylamide, N,N-diethylacrylamide, N-isopropylacrylamide, N-vinylformamide, N-vinylmethylacetamide, N-vinyl pyrrolidone, hydroxyethyl methacrylate, hydroxyethyl acrylate, hydroxypropyl acrylate, hydroxypropyl methacrylate, N-t-butylacrylamide, N-methylolacrylamide, and the like.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in "Principles of Polymer Chemistry", Cornell University Press, Ithaca, N.Y., © 1953, Chapter VII, "Determination of Molecular Weights", pp. 266-316. The RSV is measured at a given polymer concentration and temperature and calculated as follows:

$$RSV = \frac{[(\eta/\eta_o) - 1]}{c}$$

$\eta$ = viscosity of polymer solution $\eta_o$ = viscosity of solvent at the same temperature $c$ = concentration of polymer in solution The units of concentration "c" are (grams/100 ml or g/deciliter). Therefore, the units of RSV are dL/g. In this patent application, a 1.0 molar sodium nitrate solution is used for measuring RSV, unless specified. The polymer concentration in this solvent is 0.045 g/dL. The RSV is measured at 30° C. The viscosities $\eta$ and $\eta_o$ are measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dL/g. When two polymer homologs within a series have similar RSV's that is an indication that they have similar molecular weights.

"Solution polymer" means a water-soluble anionic polymer as described herein that is prepared by solution polymerization. To conduct a solution polymerization of water soluble monomers, the desired monomers are dissolved in water, generally at concentrations between 5 and 40%, along with any buffers, acid or caustic, chelants and chain transfer agents. The solution is purged with nitrogen and heated to the polymerization temperature. After the polymerization temperature is reached, one or more water soluble initiators is added. These initiators may be either of the azo type or of the redox type. Then, depending on the desired polymer characteristics, the temperature is either allowed to rise uncontrolled (adiabatic) or is controlled with cooling to remove the heat generated (isothermal). After the polymerization is complete, the solution of polymer can be removed from the reaction vessel, transferred to storage and characterized.

"Cosmetically acceptable excipient" means a non-toxic, non-irritating substance which when mixed with the anionic polymer of this invention makes the polymer more suitable to be applied to skin.

Preferred Embodiments

In a preferred aspect of this invention, anionic polymer is composed of about 10 to about 80 mole percent of 2-acrylamido-2-methyl-1-propanesulfonic acid or a base addition salt thereof and from about 90 to about 20 mole percent of one or more anionic monomers.

In another preferred aspect, the anionic monomers are selected from the group consisting of acrylic acid, methacrylic acid and styrene sulfonic acid.

In another preferred aspect, the anionic polymer is composed of about 10 to about 80 mole percent of 2-acrylamido-2-methyl-1-propanesulfonic acid or a base addition salt thereof and from about 90 to about 20 mole percent of one or more nonionic monomers.

In another preferred aspect, the anionic polymer is or acrylamide/2-acrylamido-2-methyl-1-propanesulfonic acid sodium salt copolymer.

In another preferred aspect, the anionic polymer has a molecular weight of from about 20,000 to about 5,000,000 g/mol.

In another preferred aspect, the anionic polymer is methacrylic acid/2-acrylamido-2-methyl-1-propanesulfonic acid sodium salt copolymer or acrylic acid/2-acrylamido-2-methyl-1-propanesulfonic acid sodium salt copolymer.

In another preferred aspect, the anionic polymer is methacrylic acid/2-acrylamido-2-methyl-1-propanesulfonic acid sodium salt copolymer.

In another preferred aspect, the composition further comprises one or more cosmetically acceptable excipients.

In another preferred aspect, the cosmetically acceptable excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly-N acetyl-neuraminic acid), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, starch hydroxypropyltrimoium chloride, hydroxyproyl starch phosphate, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578-611 (1994) which is incorporated entirely by reference. Complex carbohydrates can be found in Kirk-Othmer *Encyclopedia of Chemical Technology*, Fourth Edition, Vol. 4, John Wiley and Sons, NY pp. 930-948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof. The structure or representative quaternary ammonium compounds is provided in the CTFA Cosmetic Ingredient Handbook, Fifth Edition, 1988, page 40.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quatemium-18, lauralkonium chloride, olealkmonium chloride, cetylpyridinium chloride, Polyquatemium-5, Polyquaternium-6, Polyquaternium-7, Polyquatemium-10, Polyquaternium-22, Polyquaternium-37, Polyquatemium-39, Polyquatemium-47, polyquaternium-55, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine.

The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used, the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning®, Midland, Mich., USA. Additional alkyl and phenyl silicones may be employed to enhance moisturizing properties. Resins such as dimethicone (and) Trimethylsiloxysilicate, known as Dow Corning® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773.

Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethylhexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200

Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquatemium-10, Guar hydroxypropyltrimonium chloride, Starch hydroxypropyltrimonium chloride, Polyquaternium-4, Polyquatemium-5, Polyquaternium-6, Polyquaternium-7, Polyquatemium-14, Polyquaternium-15, Polyquaternium-22, Polyquaternium-24, Polyquatemium-28, Polyquatemium-32, Polyquaternium-33, Polyquaternium-36, Polyquaternium-37, Polyquaternium-39, Polyquatemium-45, Polyquaternium-47 and polymethacrylamidopropyltrimonium chloride, Polyquaternium-55 and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10-30 Alkyl Acrylate Crosspolymer, such as the Carbopol® and Pemulen® series, both available from Noveon, Inc., Cleveland, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28, available from Rohm and Haas/International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl)aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Examples of preservatives include, but are not limited to, 1,2-dibromo-2,4-dicyano butane (Methyldibromo Glutaronitrile, known as MERGUARD®, Ondeo Nalco Company, Naperville, Ill., USA), benzyl alcohol, imidazolidinyl urea, 1,3-bis(hydroxymethyl)-5,5-dimethyl-2, 3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to, buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the anionic polymer described herein and then used in the cosmetically acceptable composition of this invention. The treated pigments are then more effective as sunscreen actives and for use in color cosmetics such as make up and mascara.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include mascara, eye firming gels, shaving gels, shaving creams, aftershaves, sunscreens, after sun gels, hand and body lotions and creams, soothing gels, liquid soaps, bar soaps, bath oil bars, facial washes, body washes, hand or mechanical dishwashing compositions, shower gels, bubble baths, deodorants, anti-perspirants, and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The foregoing may be better understood by reference to the following Examples, which are presented for purposes of illustration and are not intended to limit the scope of this invention.

EXAMPLE 1

Preparation of a representative acrylic acid/2-acrylamido-2-methyl-1-propanesulfonic acid sodium salt copolymer To a 1.5-liter resin reactor equipped with stirrer, temperature controller, and water cooled condenser is added 1690.19 g of deionized water, 229.01 g of a 58% solution of the sodium salt of 2-acrylamido-2-methyl-1-propanesulfonic acid (AMPS), 80.00 g of acrylic acid and 0.20 g of EDTA. The resulting solution is sparged with 1 L/min. of nitrogen, heated to 72° C. and 0.10 g of sodium bisulfite and 0.50 g of 2,2' azobis(N,N' 2-amidinopropane) dihydrochloride (V-50, Wako Chemicals, Richmond, Va., USA) are added. Polymerization begins within 5 minutes and after 10 minutes, the solution becomes viscous and the temperature of the reaction rises to 80° C. The reaction is continued for a total of 16 hours at 78-82° C. The resulting 10% polymer solution has a Brookfield viscosity of 1000 cps at 25° C. and contains a 60/40 w/w copolymer of acrylic acid/AMPS with an intrinsic viscosity of 2.8 dL/g in 1.0 molar NaNO$_3$.

The properties of representative acrylic acid/2-acrylamido-2-methyl-1-propanesulfonic acid sodium salt (AA/AMPS) copolymers are summarized in Table 1.

TABLE 1

Properties of Representative AA/AMPS Copolymers

| Anionic Polymer | AA/AMPS (wt/wt) | AA/AMPS (mol/mol) | RSV @1.0% (dL/g) | IV (dL/g) | VISC (cps) |
|---|---|---|---|---|---|
| 1 | 60/40 | 80/20 | 3.0 | 2.8 | 1000 |
| 2 | 40/60 | 66/34 |  | 2.8 | 1000 |
| 3 | 60/40 | 81/19 |  | 2.0 | 487.5 |
| 4 | 90/10 | 90/10 |  | 3.6 | 7040 |
| 5 | 60/40 | 81/19 |  | 8.0 | 63300 |
| 6 | 60/40 | 81/19 |  | 1.9 | 19250 |

EXAMPLE 2

Preparation of a representative methacrylic acid/2-acrylamido-2-methyl-1-propanesulfonic acid copolymer To a 1.5-liter resin reactor equipped with stirrer, temperature controller, and water cooled condenser is added 939.21 g of deionized water, 191.92 g of a 58% solution of the sodium salt of 2-acrylamido-2-methyl-1-propanesulfonic acid (AMPS), 99.50 g of methacrylic acid, 92.00 g of a 50% solution of sodium hydroxide (to adjust the reaction mixture to pH=7.0) and 0.20 g of EDTA. The resulting solution is sparged with 1 L/min. of nitrogen, heated to 45° C. and 0.50 g of V-50 is added. Polymerization begins within 15 minutes and after 60 minutes, the solution becomes viscous and the temperature of the reaction rises to 50° C. The reaction is continued for 18 hours at 48-52° C. The reaction mixture is then heated to 80° C. and maintained at 78-82° C. for 24 hours. The resulting polymer solution has a Brookfield viscosity of 43200 cps at 25° C. and contains 15% of a 49/51 W/W (70/30 M/M) copolymer of methacrylic acid/AMPS with an intrinsic viscosity of 4.28 dL/gm in 1.0 molar NaNO$_3$.

The properties of representative methacrylic acid/2-acrylamido-2-methyl-1-propanesulfonic acid sodium salt (MAA/AMPS) copolymers are summarized in Table 2.

TABLE 2

Properties of Representative MAA/AMPS Copolymers

| Anionic Polymer | MAA/AMPS (wt/wt) | MAA/AMPS (mol/mol) | RSV @1.0% (dL/g) | IV (dL/g) | VISC (cps) |
|---|---|---|---|---|---|
| 7 | 62.5/37.5 | 80/20 | 8.2 | 4.3 | 61300 |
| 8 | 79/21 | 90/10 | 5.4 | 3.1 | 24375 |
| 9 | 49/51 | 70/30 | 9.1 | 4.3 | 43200 |
| 10 | 38.4/61.6 | 60/40 | 6.8 | 3.6 | 32500 |
| 11 | 29.4/70.6 | 50/50 | 7.0 | 3.6 | 31750 |
| 12 | 29.4/70.6 | 50/50 | 5.1 | 3.1 | 15100 |
| 13 | 21.7/78.3 | 40/60 | 4.3 | 2.9 | 9420 |
| 14 | 15.3/84.7 | 30/70 | 3.8 | 2.5 | 6470 |
| 15 | 9.4/90.6 | 20/80 | 3.9 | 2.5 | 8150 |

EXAMPLE 3

Preparation of a representative acrylamide/2-acrylamido-2-methyl-1-propanesulfonic acid sodium salt copolymer Into a 1.5-liter resin reactor equipped with stirrer, temperature controller, and water cooled condenser is added 225.07 g of 2-acrylamido-2-methyl-1-propanesulfonic acid sodium salt (Na-AMPS) (58% solids), 191.61 g of acrylamide (49.3% solids), 1080.70 g of deionized water, 0.50 g of a 40% solution of EDTA and 0.50 g of sodium hypophosphite. Once the monomer solution has been added, the beaker is rinsed with 600 g of deionized water and the rinse is added to the reactor. The reaction mixture is stirred and heated to 45° C. Once at 45° C., 1.13 g of a 10% wt solution of 2,2'-azobis[2-(2-imidazolin-2-yl)propane] dihydrochloride (VA-044, Wako Chemicals USA, Inc., Richmond, Va.) initiator (500 ppm based on monomer) is added and the reaction mixture is purged with nitrogen at approximately 1 L/min. After several minutes the reaction mixture becomes viscous. After approximately eight hours, the reaction mixture is cooled to room temperature and the contents are discharged. The polymer has an IV of about 2.5 dL/g and a Brookfield viscosity of about 5700 cps (15% polymer solution).

EXAMPLE 4

Clear Facial Cleanser

The facial cleanser removes dirt, grease and grime from the face. The product normally contains a mild cleansing agent, a thickener, a moisturizer and water.

The addition of polymer of this invention to clear facial cleanser formulations gives the formulation a much nicer and smooth feel and also increases the viscosity of the formulation from 330 cps to 1600 cps.

A representative clear facial cleanser composition containing an anionic polymer of this invention shown in Table 3. The composition is prepared by hydrating hydroxyethyl cellulose with water for 3 hours. A solution of Dl-panthenol in water is prepared in a separate container. The Dl-panthenol solution and the remaining ingredients are then added slowly to the hydroxyethyl cellulose solution.

TABLE 3

Representative Clear Facial Cleanser Formulation

| Ingredient | INCI Name | Weight % |
|---|---|---|
| Natrosol 250 | Hydroxyethyl cellulose | 0.60 |
| Water | Water | 60.00 |
| Bio-Terge As-40 | Sodium $C_{14-16}$ olefin sulfonate | 10.00 |
| Crotein SPC | Hydrolyzed collagen | 0.50 |
| Dl-Panthenol | dl-Panthenol | 0.20 |
| Water | Water | 10.0 |
| Propylene Glycol | Propylene glycol | 0.50 |
| Amphosol CG | Cocamidopropyl betaine | 0.50 |
| Anionic Polymer | Methacrylic acid/sodium acrylamidomethyl propane sulfonate copolymer | 5.00 |
| Versene Na 2 | Disodium EDTA | 0.05 |
| Glydant | DMDM Hydantoin | 0.10 |
| Merguard 1190 | Methyldibromo glutaronitrile and dipropylene glycol | 0.10 |
| Fragrance(Aroma dynamics 212 581-0289) | | 0.06 |
| Water | Water | Qs to 100 |

EXAMPLE 5

Eye Firming Gel

An eye firming gel composition containing a representative anionic polymer of this invention is shown in Table 4. The composition is prepared by hydrating the hydroxyethyl cellulose without heating and then adding the ingredients from Part B in the order listed, mixing well between each addition.

Eye firming gel compositions containing an anionic polymer of this invention are easier to spread onto skin and have an enhanced smooth feel compared to compositions which do not contain anionic polymer.

TABLE 4

Representative Eye Firming Gel Composition

| Part | Ingredient | INCI Name | Weight % |
|---|---|---|---|
| A | Water | Water | 89.99 |
| | Natrosol 250HHR | Hydroxyethyl cellulose | 0.50 |
| B | Anionic Polymer | Methacrylic acid/sodium acrylamidomethyl propane sulfonate copolymer | 9.00 |
| | Fancorsil ® LIM-1 | PEG-8 dimethicone meadowfoamate | 0.31 |
| | Glydant | DMDM Hydantoin | 0.10 |
| | Merguard 1190 | Methyldibromo glutaronitrile (and) dipropylene Glycol | 0.10 |

EXAMPLE 6

Clear Mascara

Clear mascara conditions lashes and brows. Clean sculpting gel sets brow color and brows in place and provides easy contouring. The clear mascara contains no tar, turpentine or shellac, won't break lashes, is smear-proof and won't flake.

A clear mascara composition containing a representative anionic polymer of this invention is shown in Table 5. The composition is prepared by neutralizing triethanolamine and then adding the rest of the ingredients in part A to the Carbomer gel. The ingredients B and C are diluted with water and added to part A.

TABLE 5

Representative Clear Mascara Composition

| Part | Ingredient | INCI Name | Weight % |
|---|---|---|---|
| A | Water | Water | 30.0 |
|  | Carbopol 980 | Carbomer | 0.70 |
|  | Triethanolamine | Triethanolamine | 0.50 |
|  | Versene 100 | Tetrasodium EDTA | 0.03 |
|  | Escalol 577 | Benzophenone-4 | 0.10 |
| B | Anionic polymer | Methacrylic acid/sodium acrylamidomethyl propane sulfonate copolymer | 1.00 (solid) |
|  | Water | Water | 30.00 |
| C | PVP K30 | PVP | 0.15 |
|  | Water | Water | 20.0 |
|  | Glydant | DMDM Hydantoin | 0.125 |
|  | Water | Water | Qs to 100 |

EXAMPLE 7

Facial Soothing Cream

Facial soothing cream softens and smoothes the skin. It forms a smooth, dry, continuous, flexible film on the skin and induces rehydration of the stratum corneum. The facial soothing cream formulation of this invention gives a soothing and cooling feel upon the application of the cream.

A facial soothing cream containing a representative anionic polymer of this invention is shown in Table 6. The composition is prepared by slowly sifting a blend of the xanthan gum and the magnesium aluminum silicate to about 80% of the water and mixing a about 400 rpm until mixture begins to hydrate and thicken. After addition is complete, the mixture is mixed at 800 rpm for at least 30 minutes to activate the magnesium aluminum silicate. A mixture of anionic polymer in the remaining water is then added and mixing is continued until the mixture is uniform. Add preservative.

TABLE 6

Representative Facial Soothing Cream

| INCI Name | Weight % |
|---|---|
| Deionized water | 80.00 |
| Magnesium aluminum silicate | 1.90 |
| Xanthan gum | 1.27 |
| Methacrylic acid/sodium acrylamidomethyl propane sulfonate copolymer | 1.00 |
| DMDM Hydantoin | 0.10 |
| Deionized water | 15.79 |
| Percent rounded | 100.06 |

EXAMPLE 8

Pearlized Liquid Hand Soap

The liquid hand soap provides cleansing function to hands. It removes grease, dirt from hands. It often contains a surfactant and moisturizer in the formulation.

A pearlized liquid hand soap composition containing a representative anionic polymer of this invention is shown in Table 7. The composition is prepared by adding each of ingredient to deionized water to mixing vessel with agitation in the order shown in Table 7, mixing well between additions. The pH is then adjusted to about 6.0.

TABLE 7

Representative Pearlized Liquid Hand Soap

| Trade Name | INCI Name | Weight. % |
|---|---|---|
| Deionized water | Deionized water | qs. to 100 |
| Standapol A | Ammonium lauryl sulfate | 20.00 |
| Standapol ES-3 | Sodium laureth sulfate | 20.00 |
| TegoBetaine L-7 | Cocamidopropyl betaine | 5.00 |
| Monamid 716 | Lauramide DEA | 2.50 |
| Crodapearl NI Liquid | Hydroxyethyl stearamide MIPA (and) PPG-5 ceteth-20 | 2.00 |
| Anionic polymer | Methacrylic acid/sodium acrylamidomethylpropane sulfonate copolymer | 1.87 |
| Citric Acid | Citric Acid | qs. to pH 6.0 |
| Glydant | DMDM Hydantoin | 0.20 |

EXAMPLE 9

Moisturizing Lotion

The moisturizing lotion composition of this invention delivers the moisture needed by skin after the application of the lotion. The lotion is usually formulated as oil-in-water emulsions of the vanishing cream type. It contains a fatty acid or fatty alcohol, which thickens the emulsion and forms the emollient film on the skin.

A moisturizing lotion composition containing an anionic polymer of this invention is shown in Table 8. The composition is prepared by slowly sifting Carbomer into water to 80° C. and mixing at 80° C. until the Carbomer is hydrated. Part B is heated to 80° C. and added to Part A with rapid agitation. Mixing is continued for 5 minutes at 80° C., the triethanolamine is added and mixing is continued until uniform (approximately 10 minutes) from heat while mixing is continued. At 40° C., the anionic polymer, methyldibromo glutaronitrile and dipropylene glycol are added and mixing is continued until uniform.

TABLE 8

Representative Moisturizing Lotion

| Part | Ingredients | INCI Name | Weight % |
|---|---|---|---|
| A | Water | Water | qs to 100 |
|  | Carbopol 980 | Carbomer | 0.20 |
| B | Glucate SS | Methyl glucose sesquisterate | 0.80 |
|  | Glucamate SSE-20 | PEG-20 Methyl glucose sesquisterate | 1.00 |
|  | Acetulan | Cetyl acetate and acetylated lanolin alcohol | 2.00 |
|  | Promulgen D | Cetearyl alcohol and Ceteareth-20 | 2.00 |
|  | Cerasynt SD | Glyceryl stearate | 0.50 |
|  | Blandol | Mineral oil | 8.00 |
| C | Triethanolamine 99% | Triethanolamine | 0.31 |
|  | Anionic polymer | Methacrylic acid/sodium acrylamidomethyl | 4.0 |

TABLE 8-continued

Representative Moisturizing Lotion

| Part | Ingredients | INCI Name | Weight % |
|---|---|---|---|
| | Merguard 1190 | propane sulfonate copolymer Methyldibromo glutaronitrile and dipropylene glycol | 0.10 |

EXAMPLE 10

Pearlized Body Wash

The pearlized body wash of this invention is a cleansing product used for body wash. It is often formulated with moisturizing ingredients that deliver softer and smoother feel to skin after the shower.

A pearlized body wash composition containing an anionic polymer of this invention is shown in Table 9. The composition is prepared by adding to water at 70-75° C. in a mixing vessel, mixing well between each addition. The temperature is maintained at 70-75° C. for 10 minutes and then lowered to about 40° C. Disolvene Na-2×disodium EDTA is added with thorough mixing and the pH is adjusted to about 6 with citric acid. with mixing and additional deionized water is added to obtain the desired concentration.

TABLE 9

Representative Pearlized Body Wash

| Trade Name | INCI Name | Weight % |
|---|---|---|
| Deionized water | Deionized water | qs. to 100 |
| Ninol M10 | Cocamide MIPA | 2.00 |
| Standapol ES-2 | Sodium laureth sulfate | 20.00 |
| Standapol WAQ-LC | Sodium lauryl sulfate | 10.00 |
| TegoBetaine L-7 | Cocamidopropyl betaine | 5.00 |
| EGMS-VA | Glycol stearate | 2.00 |
| Anionic polymer | Methacrylic acid/sodium acrylamidomethyl/propane sulfonate copolymer | 2.00 |
| Dissolvine NA-2X | Disodium EDTA | 0.10 |
| Citric Acid | Citric Acid | qs. to pH 6.0 |
| Merguard 1190 | Methyldibromo Glutaronitrile (and) Dipropylene Glycol | 0.20 |

EXAMPLE 11

After Shave Lotion

The after shave lotion composition of this invention gives the face a smooth, silky feel without a trace of greasiness or tackiness. Similar benefits can be achieved in ladies bodyfreshener and cologne-splash type products.

An after shave lotion composition containing an anionic polymer of this invention is shown in Table 10. The composition is prepared by adding the ingredients in the order shown in Table 10 with sufficient agitation to achieve a uniform blend following each addition.

TABLE 10

Representative After Shave Lotion

| Ingredients | INCI Name | Weight % |
|---|---|---|
| Ethanol 190 Proof | Alcohol | 85.0 |
| Water, D.I | Water | Qs to 100 |
| Propylene Glycol | Propylene Glycol | 1.0 |
| Anionic polymer | Methacrylic acid/sodium acrylamidomethyl propane sulfonate copolymer | 0.5 |

Cosmetic formulations containing anionic polymers are tested using the following protocols.

I. Sensory Evaluation of Slippery Feel for Clear Facial Cleanser and Moisturizing Lotion Lotion or cleanser is evaluated by panelists. The panelists squeeze down the lotion or cleanser between the index finger and thumb and then rub both fingers back and forth to feel the slipperiness. The slipperiness is rated from 1 to 5; 1 means the least slippery (water is assigned as 1) and 5 means the most slippery.

II. Sensory Testing of Facial Soothing Cream

Six panelists are trained in this evaluation where samples with and without polymer are compared. Each panelist wipes off the forearm area with isopropyl alcohol prior to each test. Approximately 75 μl are placed onto the volar forearm. After 3× and 15× rotations, the samples are evaluated. After complete rub-in, the smoothness of the dried product is evaluated. The test is run under ambient conditions (23.5° C. and >50% relative humidity).

III. Standard Hand Washing Procedure

Prior to liquid hand soap evaluation, panelists wash their hands according to the following Standard Hand Wash Procedure. On testing days, panelists can not use any lotion on hands prior to evaluation.
  1. Remove all jewelry from wrists and hands.
  2. Thoroughly wet the Ivory Soap bar and your hands with 38±1° C. tap water.
  3. Take the soap bar in both hands, rotating the bar 10 times. Set the soap bar aside.
  4. Rub hands back and forth 10 times.
  5. Rub right hand over left hand and then left hand over right hand. Repeat two times.
  6. Rinse hands thoroughly for 10 seconds and pat until dry with a paper towel.

IV. Liquid Hand Soap Evaluation

Liquid hand soaps containing an anionic polymer are evaluated for flash and ultimate lather, wet lather slip, thickness, rinse off and immediate and delayed after feel by panelists using the following protocols. Prior to testing, panelists wash their hands according to the procedure in III above. Panelist rate soap in each category on a scale of 1-10, 1 being the low end, 10 being the high end.
  1. Turn on the tap water and set the temperature to 38±1° C.
  2. Wet hands by passing them under the water three times.
  3. Shake off excess water.
  4. Apply 1.5-ml of liquid hand soap on one hand (palm).
  5. Add 2.5-ml water to same palm.

IVa. Flash and Ultimate Lather
  1. Rub hands back and forth 10 times (Sliding one palm over the other palm up and down=1 time).

2. Rotate hands 3 times. (Lightly rubbing right hand over left hand and left hand over right hand=1 rotation).
3. Place right hand around the bottom (wrist area) of the left hand. Squeeze the lather up from your left hand to the area between your index finger and thumb of your right hand. Repeat with left hand.
4. For picture purposes, tuck the left thumb in fist to show only the flash lather.
5. Record the volume, density, and bubble size of flash lather.
6. Rotate hands (as in Step 2) 5 more times.
7. Repeat Step 3.
8. For picture purposes, tuck the left thumb in fist to show only the ultimate lather.
9. Record the volume, density, and bubble size of ultimate lather.
10. Do not rinse hands.

IVb. Wet Lather Slip
1. Evaluate how slippery the liquid hand soap feels on hands.
2. Do not rinse hands.

IVc. Thickness
1. Place some of the lather between an index finger and thumb of the same hand.
2. Gently rub thumb and index finger together.
3. Determine the lather thickness.

IVd. Rinse Off
1. Rinse hands under 38±1° C. tap water.
2. Record the time it takes until hands feel completely rinsed.

IVe. Immediate After Feel
1. Dry hands with Wyp-All.
2. Evaluate the following attributes: tack/stickiness, tightness, slipperiness, amount of residue and type of residue.

IVf. Delayed After Feel
Panelists evaluate hands for the following attributes 10 minutes after drying and again at 30 minutes after drying: tack/stickiness, tightness, slipperiness, amount of residue, type of residue and suppleness.

V. Body Wash Evaluation:
Body wash containing an anionic polymer are evaluated for flash and ultimate lather, wet lather slip, thickness, rinse off and immediate and delayed after feel by panelists using the following protocols. Prior to testing, panelists wash their hands according to the procedure in III above. Panelists rate soap in each category on a scale of 1-10, 1 being the low end, 10 being the high end.
1. Wash hands using the Standardized Hand Washing Procedure.
2. Wet poof under 38° C. tap water.
3. 5-ml of body wash and 10-ml of 38° C. tap water are added to the top of the poof (panelist holds poof in both hands).
4. Squeeze the poof in both hands 25 times.
5. Squeeze lather up from the poof.
6. Place right hand around the bottom (wrist area) of the left hand. Squeeze the lather up from your left hand to the area between your index finger and thumb of your right hand. Repeat with left hand.
7. Evaluate lather for slipperiness, thickness and density (rate 1-10, 1=low end, 10=high end).
8. Note bubble size, feel of lather and perception of lather.
9. Evaluate lather for rinse off (rate 1-10, 1=low end, 10=high end).
10. Rinse poof well.

EXAMPLE 12

Facial soothing cream prepared according to the method of Example 7 is compared to a control soothing cream prepared by an identical procedure except without anionic polymer. The sensory results are evaluated by a panel using the protocols described above. The results are summarized in Table 11.

TABLE 11

Sensory Results for a Representative Facial Soothing Cream containing an Anionic Polymer

| | Control | | Anionic Polymer Composition | |
|---|---|---|---|---|
| Attribute | Average | Std Deviation | Average | Std Deviation |
| Wetness3 | 8.17 | 1.17 | 8.00 | 1.67 |
| Spread3 | 9.00 | 1.26 | 9.00 | 0.63 |
| Thickness3 | 4.83 | 2.04 | 4.33 | 1.63 |
| Tackiness3 | 4.17 | 1.17 | 2.67 | 1.37 |
| Wetness15 | 5.33 | 1.75 | 4.67 | 2.50 |
| Spread15 | 6.50 | 2.43 | 6.67 | 1.63 |
| Thickness15 | 3.83 | 1.17 | 4.67 | 1.37 |
| Tackiness15 | 5.50 | 1.05 | 4.17 | 1.47 |
| Smoothness | 5.00 | 2.76 | 6.50 | 2.43 |

As shown in Table 11, the addition of anionic polymer to the formulation shows decreased tackiness after the 3× (4.17 vs. 2.67) and 15× rub-in (5.50 vs. 4.17). There is also some indication that the addition of anionic polymer may help to improve the skin smoothness (5.00 vs. 6.50 with anionic polymer).

EXAMPLE 13

Pearlized liquid hand soap containing an anionic polymer of this invention as described in Example 8 is compared to a control composition prepared by the same procedure but that does not contain anionic polymer The sensory results are evaluated by a panel using the protocols described above. The results are summarized in Table 12.

TABLE 12

Sensory Evaluation of Pearlized Liquid Hand Soap Compositions

| Application | | Control | Anionic Polymer |
|---|---|---|---|
| Flash Lather | Vol Lath | 6.33 | 6.73 |
| | Dens. | 2.07 | 2.20 |
| | Bubble | 5.87 | 6.07 |
| Ultimate Lather | Vol Lath | 6.40 | 6.80 |
| | Dens. | 5.00 | 4.93 |
| | Bubble | 2.67 | 2.80 |
| Application | Slipperiness | 5.07 | 6.33 |
| | Thickness | 3.20 | 4.07 |
| | Rinse Off | 7.00 | 6.27 |
| Immediate After Feel | Slipperiness | 3.07 | 3.20 |
| | Stickiness | 2.20 | 2.13 |
| | Suppleness | 5.53 | 5.80 |
| | Residue | 2.83 | 2.92 |
| 10-min Delayed After Feel | Slipperiness | 5.33 | 4.80 |
| | Stickiness | 1.00 | 1.00 |
| | Suppleness | 3.57 | 3.20 |
| | Residue | 1.25 | 1.42 |

The composition containing the anionic polymer unexpectedly enhances the volume, density and bubble size of the flash lather over the control. The anionic polymer continues to enhance volume in the ultimate lather. As Table 12 indicates, the anionic polymer also positively enhances slipperiness and thickness of the lather. This can be perceived to be a more luxurious lather. The composition apparently also shows positive suppleness in the "immediate after feel" stage. The results in Table 12 illustrate that anionic polymer is suitable for use in skin care compositions such as hand soap, liquid shower gel or body wash.

EXAMPLE 14

Moisturizing lotion compositions containing an anionic polymer of this invention as described in Example 9 are compared to a control composition prepared by the same procedure but that does not contain anionic polymer The sensory results are evaluated by a panel using the protocols described above. The results are summarized in Table 13.

TABLE 13

Sensory Evaluation of Moisturizing Lotion Compositions containing a Representative Anionic Polymer

|  | 0% anionic polymer | 2% anionic polymer | 4% anionic polymer |
| --- | --- | --- | --- |
| Average Rating for Slippery Feel | 2.2 | 3.8 | 4.8 |

As shown in Table 13, the slippery feel of the lotion increases as the level of the Fixomer in the lotion increases.

EXAMPLE 15

A pearlized body wash composition containing an anionic polymer of this invention as described in Example 10 is compared to a control composition prepared by the same procedure but that does not contain anionic polymer. The sensory results are evaluated by a panel using the protocols described above. The results are summarized in Table 14.

TABLE 14

Sensory Evaluation of a Pearlized Body Wash Composition containing a Representative Anionic Polymer

| Attribute | Body Wash with anionic polymer | Control |
| --- | --- | --- |
| Thickness | 6 | 4 |
| Slipperiness | 5 | 4 |
| Rinse off | 7 | 7 |

As shown in Table 14, the composition containing anionic polymer has enhanced properties. The body wash gives a more luxurious, creamy lather with good density. The lather has small bubble size and good slip and thickness, which is perceived as being more luxurious by a consumer.

The addition of anionic polymer also increases the body wash viscosity from 4,100 cps (without anionic polymer) to 6,300 cps (with anionic polymer).

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

The invention claimed is:

1. A method of treating skin, wherein said treatment imparts lubricity or silkiness to the skin, comprising applying a cosmetically acceptable composition to the skin comprising about 0.1 to about 20 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic monomers or nonionic water soluble monomers.

2. The method of claim 1 wherein said anionic polymer is composed of about 10 to about 80 mole percent of 2-acrylamido-2-methyl-1-propanesulfonic acid or abase addition salt thereof and from about 90 to about 20 mole percent of one or more anionic monomers.

3. The method of claim 2 wherein said anionic monomers are selected from the group consisting of acrylic acid, methacrylic acid and styrene sulfonic acid.

4. The method of claim 1 wherein said anionic polymer is composed of about 10 to about 80 mole percent of 2-acrylamido-2-methyl-1-propanesulfonic acid or a base addition salt thereof and from about 90 to about 20 mole percent of one or more nonionic water soluble monomers.

5. The method of claim 4 wherein said anionic polymer is acrylarnide/2-acrylamido-2-methyl-1-propanesulfonic acid sodium salt copolymer.

6. The method of claim 1 wherein said anionic polymer has a molecular weight of from about 20,000 to about 5,000,000 g/mol.

7. The method of claim 2 wherein said anionic polymer is methacrylic acid/2-acrylamido-2-methyl-1-propanesulfonic acid sodium salt copolyiner or acrylic acid/2-aerylamido-2-methyl-1-propanesulfonic acid sodium salt copolymer.

8. The method of claim 2 wherein said anionic polymer is methacrylic acid/2-acrylamido-2-methyl-1-propanesulfonic acid sodium salt copolymer.

9. The method of claim 8 wherein said cosmetically acceptable composition comprises from about 0.5 to about 10 weight percent, based on polymer solids, of the anionic polymer.

10. The method of claim 1 wherein said cosmetically acceptable composition further comprises one or more cosmetically acceptable excipients.

11. The method of claim 10 wherein said excipients are selected from the group consisting of water, saccharides, surface active agents, humectants, petrolatum, mineral oil, fatty alcohols, fatty ester emollients, waxes and silicone-containing waxes, silicone oil; silicone fluid, silicone surfactants, volatile hydrocarbon oils, quaternary nitrogen compounds, amine functionalized silicones, conditioning polymers, rheology modifiers, antioxidants, sunscreen active agents, di-long chain sniffles from about $C_{10}$ to $C_{22}$, long chain fatty amines from about $C_{10}$ to $C_{22}$, fatty alcohols, ethoxylated fatty alcohols and di-tail phospholipids.

12. The method of claim 1 wherein said cosmetically acceptable composition is selected from the group consisting of mascara, eye firming gels, shaving gels, shaving creams, aftershaves, sunscreens, after sun gels, hand and body lotions and creams, soothing gels, liquid soaps, bar soaps, bat oil bars, facial washes, body washes, hand or mechanical dishwashing compositions, shower gels, bubble baths, deodorants and anti-perspirants.

13. The method of claim 12 wherein said cosmetically acceptable composition is selected from the group consisting of facial washes and body washes.

\* \* \* \* \*